US005545716A

United States Patent [19]
Johnson et al.

[11] Patent Number: 5,545,716
[45] Date of Patent: Aug. 13, 1996

[54] SUPERANTIGEN AGONIST AND ANTAGONIST PEPTIDES

[75] Inventors: Howard M. Johnson, Gainesville, Fla.; Carol H. Pontzer, Silver Spring, Md.; Nathan D. Griggs, Charlottesville, Va.

[73] Assignee: University of Florida, Gainesville, Fla.

[21] Appl. No.: 220,378

[22] Filed: Mar. 29, 1994

Related U.S. Application Data

[63] Continuation-in-part of Ser. No. 941,497, Sep. 8, 1992, abandoned.

[51] Int. Cl.$^6$ ........................................... A61K 38/16
[52] U.S. Cl. ........................ 530/324; 530/325; 530/326
[58] Field of Search ....................... 514/12, 13; 530/324, 530/325, 326; 435/882

[56] References Cited

PUBLICATIONS

Huang J Biol Chem 262, 7006, 1987.
Betley J. Bacteriol 170, 34–41, 1988.
Johnson, H. M., H. I. Magazine (1988) "Potent Mitogenic Activity of Staphylococcal Enterotoxin A Requires Induction of Interleukin 2" Int. Arch. Allergy Appl. Immunol. 87:87–90.
Carlsson, R. etal. (1988) "Binding of Staphylococcal Enterotoxin A to Accessory Cells is a Requirement for its Ability to Activate Human T Cells" The Journal of Immunology 140(8):2484–2488.
Fleischer, B., H. Schrezemeier (1988) "T Cell Stimulation by Staphylococcal Enterotoxins" J. Exp. Med. 167:1697–1707.
Mollick, J. A. et al. (1989) "Class II MHC Molecules Are Specific Receptors for Staphylococcus Enterotoxin A" Science 244:817–820.
Janeway, C. A. Jr. et al. (1989) "T–Cell Responses to Mls and to Bacterial Proteins that Mimic its Behavior" Immunological Reviews 107:61–88.
White, J. et al. (1989) "The Vβ–Specific Superantigen Staphylococcal Enterotoxin B: Stimulation of Mature T Cells and Clonal Deletion in Neonatal Mice" Cell 56:27–35.
Herman, A. et al. (1991) "Superantigens: Mechanism of T–Cell Stimulation and Role in Immune Responses" Ann. Rev. Immunol. 9:745–772.
Kawabe, Y., A. Ochi (1991) "Programmed cell death and extrathymic reduction of Vβ8+ CD4+T cells in mice tolerant ot *Staphylococcus aureus* enterotoxin B" Nature 349:245–248.
Kawabe, Y., A. Ochi (1990) "Selective Anergy of vβ8+, CD4+T Cells in Straphylococcus Enterotoxin B–primed Mice" J. Exp. Med. 172:1065–1070.

Rellahan, B. L. et al. (1990) "In vivo Induction of anergy in Peripheral Vβ8+T Cells by Staphylococcal Enterotoxin B" The Journal of Experimental Medicine 172:1091–1100.
Fischer, H. et al. (1990) "Production of TNF–α and TNF–β by Staphylococcal Enterotoxin A Activated Human T Cells" Journal of Immunology 144(12):4663–4669.
Gjorloff, A. et al. (1991) "Induction of Interleukin–1 in Human Monocytes by the Superantigen Staphlococcal Enterotoxin A Requires the Participation of T Cells" Cellular Immunology 137:61–71.
Scholl, P. R. et al. (1992) "Role of Protein Tyrosine Phosphorylation in Monokine Induction by the Staphylococcal Superantigen Toxic Shock Syndrome Toxin–1" The Journal of Immunology 148(7):2237–2241.
Yokota, S. et al. (1988) "Enhancement of Antigen– and Mitogen–Induced Human T Lymphocyte Proliferation by Tumor Necrosis Factor–α" The Journal of Immunology 140(2):531–536.
Griggs, N. D. et al. (1992) "Mapping of Multiple Binding Domains of the Superantigen Staphylococcal Enterotoxin A for HLA" The Journal of Immunology 148(8):2516–2521.
Acha–Orbea, H. et al. (1988) "limited Heterogeneity of T Cell REceptors from Lymphocytes Mediating Autoimmune Encephalomyelitis Allows Specific Immune Intervention" Cell 54:263–273.
Offner, H. et al. (1991) "T Cell REceptor Peptide Therapy Triggers Autoregulation of Experimental Encephalomyelitis" Science 251:430–432.
Kim, C. et al. (1991) "Reduction of Lupus Nephritis in MRL/lpr Mice by a Bacterial Superantigen Treatment" J. Exp. Med. 174:1431–1437.
Grossman, D. et al. (1990) "Dissociation of the Stimulatory Activities of Staphylococcal Enterotoxins for T Cells and Monocytes" J. Exp. Med. 172:1831–1841.
Grossman, D. et al. (1991) "Mutation of the Disulfide Loop in Staphylococcal Enterotoxin A" The Journal of Immunology 147(10):3274–3261.
Pontzer, C. H. et al (1989) "Localization of an Immune Functional Site on Staphylococcal Enterotoxin A Using the Synthetic Peptide Approach" The Journal of Immunology 143(1):280–284.
Pontzer, C. H. et al. (1990) "Site of Nonrestrictive Binding of SEA to Class II MHC Antigens" Int. Arch. Allegy Appl. Immunol. 93:107–112.

*Primary Examiner*—Jill Warden
*Assistant Examiner*—David Lukton
*Attorney, Agent, or Firm*—Saliwanchik & Saliwanchik

[57] ABSTRACT

The subject invention concerns novel peptide agonists and antagonists of staphylococcal enterotoxin A. Specifically exemplified are peptide agonists which stimulate T cell proliferation.

4 Claims, 7 Drawing Sheets

| Donor | 1-45 | 39-66 | 62-86 | 83-104 | 102-124 | 121-149 | 146-173 | 166-193 | 189-217 | 211-233 |
|---|---|---|---|---|---|---|---|---|---|---|
| 1 | 4637 | 10878 | 5514 | 57860 | 2786 | 25847 | 3977 | 3748 | 4014 | 3071 |
| 2 | 6283 | 64122 | 3358 | 16444 | 1631 | 7847 | 1879 | 1342 | 1135 | 1468 |
| 3 | 5328 | 721 | 4320 | 4095 | 5354 | 30120 | 6287 | 4181 | 3335 | 4133 |
| 4 | 6528 | 4044 | 5384 | 6617 | 3863 | 47773 | 3315 | 5943 | 3052 | 3308 |

Figure 7

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Ser Glu Lys Ser Glu Glu Ile Asn Glu Lys Asp Leu Arg Lys Lys Ser
 1               5                  10                      15
Glu Leu Gln Gly Thr Ala Leu Gly Asn Leu Lys Gln Ile Tyr Tyr Tyr
                20                  25                  30
Asn Glu Lys Ala Lys Thr Glu Asn Lys Glu Ser His Asp
            35                  40                  45
```

( 2 ) INFORMATION FOR SEQ ID NO:2:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

```
Glu Asn Lys Glu Ser His Asp Gln Phe Leu Gln His Thr Ile Leu Phe
 1               5                  10                      15
```

```
              Lys  Gly  Phe  Phe  Thr  Asp  His  Ser  Trp  Tyr  Asn  Asp
                             20                       25
```

( 2 ) INFORMATION FOR SEQ ID NO:3:

( i ) SEQUENCE CHARACTERISTICS:
    ( A ) LENGTH: 25 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:3:

```
    Ser  Trp  Tyr  Asn  Asp  Leu  Leu  Val  Asp  Phe  Asp  Ser  Lys  Asp  Ile  Val
     1              5                        10                            15
    Asp  Lys  Tyr  Lys  Gly  Lys  Lys  Val  Asp
                   20                      25
```

( 2 ) INFORMATION FOR SEQ ID NO:4:

( i ) SEQUENCE CHARACTERISTICS:
    ( A ) LENGTH: 22 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

```
    Lys  Lys  Val  Asp  Lys  Tyr  Gly  Ala  Tyr  Tyr  Gly  Tyr  Gln  Cys  Ala  Gly
     1              5                        10                            15
    Gly  Thr  Pro  Asn  Lys  Thr
                   20
```

( 2 ) INFORMATION FOR SEQ ID NO:5:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

```
    Asn  Lys  Thr  Ala  Cys  Met  Tyr  Gly  Gly  Val  Thr  Leu  His  Asp  Asn  Asn
     1              5                        10                            15
    Arg  Leu  Thr  Glu  Glu  Lys  Lys
                   20
```

( 2 ) INFORMATION FOR SEQ ID NO:6:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:6:

```
    Glu  Glu  Lys  Lys  Val  Pro  Ile  Asn  Leu  Trp  Leu  Asp  Gly  Lys  Gln  Asn
     1              5                        10                            15
    Thr  Val  Pro  Leu  Glu  Thr  Val  Lys  Thr  Asn  Lys  Lys  Asn
                   20                      25
```

( 2 ) INFORMATION FOR SEQ ID NO:7:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

```
Asn Lys Lys Asn Val Thr Val Gln Glu Leu Asp Leu Gln Ala Arg Arg
 1               5                  10                  15
Tyr Leu Gln Glu Lys Tyr Asn Leu Tyr Asn Ser Asp
                20                  25
```

( 2 ) INFORMATION FOR SEQ ID NO:8:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:8:

```
Lys Tyr Asn Leu Tyr Asn Ser Asp Val Phe Asp Gly Lys Val Gln Arg
 1               5                  10                  15
Gly Leu Ile Val Phe His Thr Ser Thr Glu Pro Ser
                20                  25
```

( 2 ) INFORMATION FOR SEQ ID NO:9:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:9:

```
Ser Thr Glu Pro Ser Val Asn Tyr Asp Leu Phe Gly Ala Gln Gly Gln
 1               5                  10                  15
Tyr Ser Asn Thr Leu Leu Arg Ile Tyr Arg Asp Asn Lys
                20                  25
```

( 2 ) INFORMATION FOR SEQ ID NO:10:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:10:

```
Arg Ile Tyr Arg Asp Asn Lys Ser Ile Asn Ser Glu Asn Met His Ile
 1               5                  10                  15
Asp Ile Tyr Leu Tyr Thr Ser
                20
```

SUPERANTIGEN AGONIST AND ANTAGONIST PEPTIDES

This invention was made with government support under National Institutes of Health grant number AI25904. The government has certain rights in this invention.

CROSS-REFERENCE TO A RELATED APPLICATION

This is a continuation-in-part of application Ser. No. 07/941,497, filed Sep. 8, 1992, now abandoned.

BACKGROUND OF THE INVENTION

Normally, when a person's immune system encounters a protein made by a virus or other microbe, fewer than one in 10,000 of the white blood cells known as T lymphocytes react. Although their number is small, these T lymphocytes orchestrate an attack that specifically targets the alien protein, or antigen, without harming healthy tissue. In contrast, proteins called superantigens highly activate the immune system and can cause an unproductive, even destructive, immune response.

Superantigens are the most powerful T cell mitogens known (Johnson, H. M., H. I. Magazine [1988] $Int. Arch. Allergy Appl. Immunol.$ 87:87–90). As explained below, these unique antigens stimulate T cells by first binding to class II major histocompatibility (MHC) molecules (Carlsson, R., H. Fischer, H. O. Sjogren [1988] $J. Immunol.$ 140:2484–2488; Fleischer, B., H. Schrezenmeier [1988] $J. Exp. Med.$ 167:1697–1707; Mollick, J. A., R. G. Cook, R. R. Rich [1989] $Science$ 244:817–820) and then as a binary complex bind in a $V_\beta$ specific manner to the T cell antigen receptor (TCR) (Janeway, C. A., J. Yagi, P. J. Conrad, M. E. Katz, B. Jones, S. Vroegop, S. Buxser [1989] $Immunol. Rev.$ 107:61–88; White, J., A. Herman, A. M. Pullen, R. Kubo, J. W. Kappler, P. Marrack [1989] $Cell$ 56:27–35).

Superantigens can arouse as many as one in five T cells, most of which are useless for fighting a current infection. What is worse, certain of the activated cells may unleash an autoimmune attack which targets tissues of the host organism. At times, superantigens may even have the opposite effect: they somehow trigger the death of the cells they excite.

Scientists have gleaned much of what they understand about superantigens from studying the earliest known examples: a group of structurally related proteins called staphylococcal enterotoxins. Staphylococcal enterotoxins account for as much as 45 percent of all cases of food poisoning. It is well established that when strains of the bacterium $Staphylococcus aureus$ colonize food, they secrete one or more enterotoxins, which are now named alphabetically as A, B, C, D, and E. Within hours after people ingest badly contaminated, toxin-laden food, they begin to feel weak, feverish, and nauseated. Interestingly, intestinal tissue of affected patients looks virtually normal under the microscope. The only obvious abnormality is the presence of white cells in the tissue. It has now also been found that introduction of an enterotoxin to blood triggers the proliferation of lymphocytes. Just a few hundred molecules of toxin triggers a degree of replication that surpasses what could be achieved by a billion copies of a conventional antigen—for example, a protein on the influenza virus.

Further research has documented that a small amount of an enterotoxin can yield extraordinarily high production of cytokines, which are produced by the subset of T lymphocytes called helper cells. These cells direct much of the immune response. The helper cells do not attack microbes themselves; instead they rely on chemical signals known as cytokines to activate both cytotoxic T lymphocytes, which kill infected cells, and B lymphocytes, which secrete antibodies against antigens.

By the mid-1980s it was recognized that when a tiny amount of enterotoxin A was mixed with T lymphocytes, the collection of cells produced a huge quantity of the cytokine known as interleukin-2 (IL-2). It has also been determined that infusion of high doses of IL-2 into the circulation of cancer patients (as part of an experimental therapy) causes the very symptoms associated with food poisoning. These data indicate that enterotoxins make people ill by stimulating production of high levels of interleukin-2.

Before helper T cells can recognize conventional protein antigens, the proteins must first undergo processing by macrophages or other antigen-presenting cells. These cells engulf antigens and process them into peptides. The presenters then display the peptide antigens at the cell surface in combination with major histocompatibility complex (MHC) class II molecules. A peptide fits in a cleft on an MHC molecule. Once an antigen is displayed, the few helper cells in the body that bear receptors for the particular peptide link up with it. Each T cell is specific for one kind of peptide antigem Like conventional toxins, enterotoxin superantigens can arouse helper cells only if antigen-presenting cells display the proteins to the T cells. Moreover, it is MHC class II molecules that do the presenting. Yet, unlike typical antigens, the enterotoxins bind MHC molecules directly; they do not require uptake and processing. Also, enterotoxins do not bind to the inner surface of the peptide-recognizing pocket of the MHC molecule, attaching instead to its outer surface. Then the MHC-superantigen unit contacts the T cell receptor at a site distinct from the surface that envelops conventional antigens. To be more precise, T cell receptors consist of two protein chains, alpha and beta. Both chains include structurally invariant and variable regions that participate in the binding of conventional peptide antigens. The enterotoxins are thought to link up with the beta-chain variable—or V-beta ($V_\beta$)-region, at a part not involved in the binding of typical antigens.

Each enterotoxin interacts with particular $V_\beta$ types. For instance, one enterotoxin may be recognized by the variable types numbered 5 and 12, whereas another might be recognized by types 12, 15, and 18. For example, SEB has been shown to be specific for T cells bearing $V_\beta$ elements such as 7 and 8.1–8.3 in mice (Herman, A., J. W. Kappler, P. Marrack, A. M. Pullen [1991] $Ann. Rev. Immunol.$ 9:745–772). Investigators estimate that every human has fewer than 30 $V_\beta$ types, although the fraction of helper T cells carrying any given type can differ from person to person. A conventional antigen can activate only the relatively few helper cells specific for that antigen. A given enterotoxin, however, can activate many times that number of helpers (having a huge variety of peptide-antigen specificities) as long as the T cells bear selected $V_\beta$ types.

Although superantigens are suspected of, at times, causing over-activation of the immune system, some evidence suggests that superantigens may also depress the immune system. T cell clones aroused by superantigens often disappear (depletion) or become inactive (anergy) after being stimulated. Staphylococcal enterotoxins, the prototype superantigens, activate T cells bearing specific T cell antigen receptor β-chain variable region elements. Their $V_\beta$ specificity has profound implications with regard to expansion, anergy, and deletion of various T cell populations in terms of immunologic disease. It has been demonstrated that although an initial mitogenic effect is observed after in vivo administration of staphylococcal enterotoxin B (SEB), the lasting result appears to be both clonal anergy and deletion of $V_\beta$ specific peripheral T cells (Kawake, Y., A. Ochi [1991] *Nature* 349:245–248; Kawake, Y., A. Ochi [1990] *J. Exp. Med.* 172:1065–1070; Rellahan, B. L., L. A. Jones, A. M. Kruisbeek, A. M. Fry, L. A. Matis [1990] *J. Exp. Med.* 172:1092–1100).

Thus far, we have primarily focused on the interaction between superantigens and helper T cell activity; however, the possible deranging effects of superantigens on B cells should not be ignored. *Staphylococcal enterotoxins* sometimes enhance antibody production by B cells and sometimes inhibit it, depending on the initial state of immune arousal. Enhancement and suppression may each be destructive. Inhibition of antibody production can depress immune functioning. Overzealous production can lead to immune complex disorders, in which antibodies attract various components of the immune system to healthy tissue, clogging them and impeding normal function.

Interaction of the staphylococcal enterotoxins with class II molecules induces production of the cytokines tumor necrosis factor alpha (TNFα) and interleukin-1 (IL-1) by monocytes (Fischer, H., M. Dohlsten, U. Andersson, G. Hedlund, P. Ericsson, J. Hansson, H. O. Sjögren [1990] *J. Immunol.* 144:4663; Gjörloff, A., H. Fischer, G. Hedlund, J. Hansson, J. S. Kenney, A. C. Allison, H. O. Sjögren, M. Dohlsten [1991] *Cell Immunol.* 137:61). Both SEA and the related toxic shock syndrome toxin one (TSST-1) are potent inducers of TNFα and IL-1. Binding of these superantigens to MHC transduces a signal through the monocyte membrane which leads to tyrosine kinase activation and phosphorylation of multiple cytoplasmic proteins and monokine gene induction (Scholl, P. R., N. Trede, T. A. Chatila, R. S. Geha [1992] *J. Immunol.* 148:2237). Subsequently, monokines can have effects on T cells; for example, TNFα can further enhance human T cell proliferation (Yokota, S., T. D. Geppert, P. E. Lipsky [1988] *J. Immunol.* 140:531). IL-1 is an additional stimulator by increasing IL-2 secretion and IL-2 receptor expression. Both IL-1 and TNFα secretion may require the presence of T cells, particularly CD4+ 45RO+ memory T cells (Fischer et al., supra; Gjörloff et al., supra). A variety of peptide sequences of the superantigen SEA that participate in binding to the class II MHC molecules have previously been studied (Pontzer, C. H., J. K. Russell, H. M. Johnson [1989] *J. Immunol.* 143:280; Pontzer, C., J. K. Russell, M. A. Jarpe, H. M. Johnson [1990] *Int. Arch. Allergy Appl. Immunol.* 93:107; Griggs, N. D., C. H. Pontzer, M. A. Jarpe, H. M. Johnson [1992] *J. Immunol.* 148:2516; Grossman, D., R. G. Cook, J. T. Sparrow, J. A. Mollick, R. R. Rich [1990] *J. Exp. Med.* 172:1831; Grossman, D., M. Van, J. A. Mollick, S. K. Highlander, R. R. Rich [1991] *J. Immunol.* 147:3274).

Superantigens have been hypothesized to be associated with a number of pathological conditions. For example, superantigens may be associated with retroviruses such as mouse mammary tumor virus and possibly the virus responsible for AIDS. Further, superantigen alteration of the T cell repertoire has import for immunodeficiency and autoimmunity. T cells bearing certain $V_\beta$ types have been implicated in various autoimmune conditions, including arthritis, lupus, and multiple sclerosis. It is conceivable, but not yet established, that over-activation of T cells by superantigens could play a role in certain autoimmune disorders.

Multiple sclerosis (MS) is a chronic, often disabling disease that attacks the central nervous system, damaging the protective coating that surrounds nerve fibers. Its symptoms can range from mild tingling sensations to problems with vision, balance and coordination— and sometimes even to paralysis. MS affects as many as 350,000 Americans, two thirds of them women.

Involvement of a predominant $V_\beta$ specific T cell population has been suggested for certain animal models of autoimmune disease. For example, experimental allergic encephalomyelitis (EAE) is an animal model for multiple sclerosis. EAE is mediated by $V_\beta 8.2^+$, CD4+T cells in PL/J mice after injection with myelin basic protein (MBP). This limited heterogeneity of TCR usage has implicated the involvement of $V_\beta 8.2^+$, CD4+T cells in EAE in PL/J mice immunized with rat myelin basic protein (Acha-Orbea, H., D. J. Mitchell, L. Timmerman, D. C. Wraith, G. S. Tausch, M. K. Waldon, S. S. Zamvil, H. O. McDevitt, L. Steinman [1988] *Cell* 54:263–273).

Recently, several novel immunological approaches have been explored relevant to autoimmune diseases such as EAE in mice and rats and lupus nephritis in MRL/lpr mice. Many have been directed toward blocking the function of the effector CD4+T cell which has been shown to exhibit $V_\beta$ isotype restriction in EAE. These approaches have included the use of anti-TCR antibodies (Acha-Orbea et al., supra), synthetic TCR peptides (Offner, H., G. A. Hashim, A. A. Vandenbark [1991] *Science* 251:430–432) and superantigen treatment (Kim, C., K. A. Siminovitch, A. Ochi [1991] *J. Exp. Med.* 174:1431–1437).

BRIEF SUMMARY OF THE INVENTION

The subject invention concerns the discovery of peptide agonists of the staphylococcal enterotoxin A (SEA). These peptides interact with appropriate T cell receptors and, instead of reducing T cell activation by blocking subsequent binding of full length SEA, these peptides are surprisingly and advantageously able to activate T cells in the absence of full length SEA.

Specifically, we have identified a segment of the staphylococcal enterotoxin A (SEA) molecule, SEA(39–66), which is able to stimulate proliferation of human T cells and demonstrates a similar $V_\beta$ expansion profile as that noted with SEA. Two additional peptides, SEA(83–104) and SEA(12–149), also display T cell stimulatory activity. The ability of peptide superantigen agonists to expand and alter the T cell repertoire has implications for the treatment of a variety of immunologic diseases such as immunodeficiency and autoimmunity.

In addition to alteration of T cell function, we have discovered a superantigen peptide agonist which activates monocytes. The peptide SEA(121–149) alone binds directly to the monocyte surface and can induce monocyte production of both tumor necrosis factor α (TNFα) and interleukin-1 (IL-1). At a concentration of 100 μM, SEA(121–149) induces 60% of the TNFα production seen with the whole SEA molecule. Thus, SEA(121–149) is an agonist for superantigen monocyte stimulatory activity. While immunotherapy using whole staphylococcal enterotoxin molecule could produce nonspecific effects and potentially undesirable side effects, peptide agonists of superantigen function can target components of the immune system, alter function, and achieve therapeutic ends.

BRIEF DESCRIPTION OF THE SEQUENCES

SEQ ID NO. 1 is the amino acid sequence of an SEA peptide designated SEA (1–45).

SEQ ID NO. 2 is the amino acid sequence of an SEA peptide designated SEA (39–66).

SEQ ID NO. 3 is the amino acid sequence of an SEA peptide designated SEA (62–86).

SEQ ID NO. 4 is the amino acid sequence of an SEA peptide designated SEA (83–104).

SEQ ID NO. 5 is the amino acid sequence of an SEA peptide designated SEA (102–124).

SEQ ID NO. 6 is the amino acid sequence of an SEA peptide designated SEA (121–149).

SEQ ID NO. 7 is the amino acid sequence of an SEA peptide designated SEA (146–173).

SEQ ID NO. 8 is the amino acid sequence of an SEA peptide designated SEA (166–193).

SEQ ID NO. 9 is the amino acid sequence of an SEA peptide designated SEA (189–217).

SEQ ID NO. 10 is the amino acid sequence of an SEA peptide designated SEA (211–233).

DETAILED DESCRIPTION OF THE INVENTION

We have identified regions on the superantigen molecule, staphylococcal enterotoxin A (SEA), that are able to stimulate human peripheral blood lymphocytes to proliferate. We have also identified a sequence of SEA which can bind human class II MHC molecules and induce monokine production. The peptide which induces monokine production, SEA(121-149), acts as a potent agonist, binding to class II MHC and activating monocytes for cytokine production. The peptides described herein are particularly advantageous because they facilitate specific manipulation of the immune system. Because of the involvement of autoimmune processes in various disease states such as diabetes, multiple sclerosis, lupus, and rheumatoid arthritis, the peptides of the subject invention provide advantageous therapeutic agents. These peptides may also be useful in treating autoimmune disorders.

While several of the SEA peptides of the subject invention are involved in binding to class II MHC, only SEA(121-149) (SEQ ID NO. 6) was capable of acting as an agonist for monokine production. In fact, we demonstrated direct binding of the synthetic peptide SEA(121-149) to monocytes. The peptide binding was inhibited by SEA, suggesting that SEA(121-149) exerts its agonist effects via binding to an SEA superantigen site on the MHC molecule.

As described in more detail below, we produced peptides corresponding to the complete amino acid sequence of SEA: SEA(1–45) (SEQ ID NO. 1), SEA(39–66) (SEQ ID NO. 2), SEA(62–86) (SEQ ID NO. 3), SEA(83–104) (SEQ ID NO. 4), SEA (102–124) (SEQ ID NO. 5), SEA(121–149) (SEQ ID NO. 6), SEA(146–173) (SEQ ID NO. 7), SEA(166–193) (SEQ ID NO. 8), SEA(189–217) (SEQ ID NO. 9), and SEA(211–233) (SEQ ID NO. 10). These peptides are shown in the Sequence Listing herein.

Figure 7:
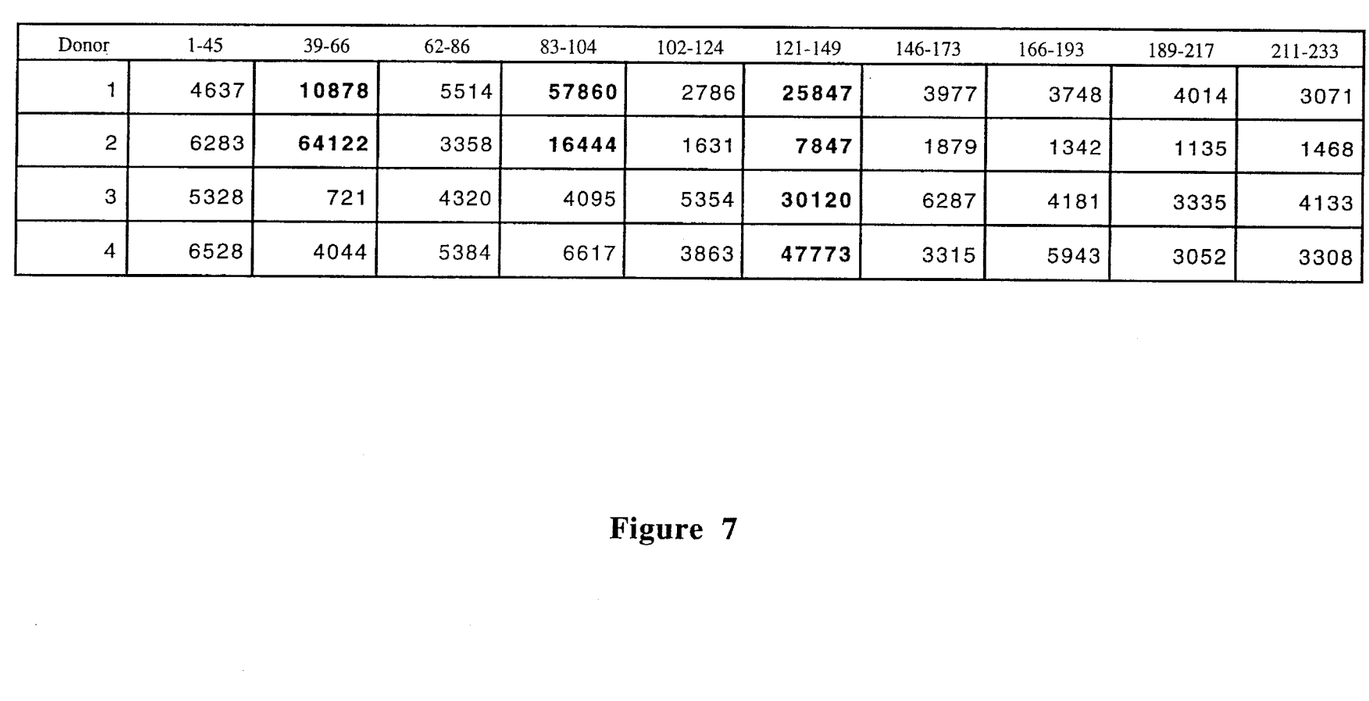
FIG. 7. Ability of peptides to stimulate human T cells to proliferate. Proliferation of HPBL from various donors was performed in the presence of 100 μM peptide. Results are expressed as the mean of six replicates. SEA at a concentration of 10 pg/ml gave approximately 80,000 cpm. Values which are significantly different from background are in bold print.

Our peptides were then tested for their ability to stimulate human T cells to proliferate. SEA(39–66) (SEQ ID NO. 2), SEA(83–104) (SEQ ID NO. 4), and SEA(121–149) (SEQ ID NO. 6) showed marked proliferation of T cells in half of the subjects, while in the other half, SEA(121–149) (SEQ ID NO. 6) alone stimulated T cells to proliferate (FIG. 7). Additionally, SEA(39–66) (SEQ ID NO. 2) was able to stimulate proliferation at concentrations as low as 30 μM. Also, SEA(39–66) (SEQ ID NO. 2) was able to specifically expand V$_β$5a⁺ T and V$_β$8+T cells which express V 8⁺ SEA sensitive V$_β$ elements. These peptides are capable of recognizing both MHC molecules and the T cell antigen receptor and, thus, afford powerful tools for modulation of the immune response.

In addition to being some of the most potent T cell mitogens, known, the staphylococcal enterotoxins activate monocytes. The toxins, such as SEA, bind to class II MHC molecules on the monocyte surface and stimulate them to produce the cytokines TNFα and IL-1. The ability of our SEA synthetic peptides to bind directly to class II MHC molecules and subsequently induce monokine production has been examined. Of several peptides that block SEA binding to receptor, only one peptide, SEA(121–149) (SEQ ID NO. 6), induces TNFα production by human peripheral blood mononuclear cells at a concentration as low as 30 μM. The cytotoxic activity was confirmed as TNFα by neutralization with anti-human TNFα antibody. Similar to SEA, optimal concentrations of SEA(121–149) also induce greater than 1,400 units/ml of IL-1. Consistent with its effects on monocyte function, SEA(121–149) binds directly to the monocyte surface, and its binding is inhibited specifically by native SEA. Further, polyclonal antibody to SEA(121–149) inhibited induction of TNFα by both SEA and toxic shock syndrome toxin one (TSST-1). This is consistent with our data showing that SEA(121–149) inhibits binding of TSST-1 to human cells, which suggests structural similarity of the regions on SEA and TSST-1 that are involved in induction of TNFα. Thus, we have identified SEA(121–149) as a peptide agonist of SEA monocyte stimulatory activity.

Toxic shock syndrome toxin one (TSST-1) is another staphylococcal enterotoxin and is an effective stimulator of TNFα from macrophages and monocytes (Fast, D. J., P. M. Schlievert, R. D. Nelson [1988] *J. Immunol.* 140:949). In fact, TSST-1 induced TNFα has been shown to inhibit polymorphonuclear leukocyte migration to sites of inaction, thereby contributing to the observed toxic effects (Fast et al., supra). We have previously shown that SEA can block TSST-1 binding; therefore, the toxins interact with MHC class II at a shared site (Pontzer, C. H., J. K. Russell, H. M. Johnson [1991] *Proc. Natl. Acad. Sci. USA* 88:125). Yet, this site is distinct from that which binds the N-terminal region of SEA. The SEA synthetic peptide, SEA(121–149) (SEQ ID NO. 6), which acts as an SEA agonist on monocytes according to the subject invention, can inhibit the binding of both SEA and TSST-1 to MHC. Thus, the common site on the MHC molecule for both toxins will bind the peptide SEA(121–149).

As stated above, TNFα induction by both SEA and TSST-1 was found to be inhibited by polyclonal antisera to SEA(121–149) (SEQ ID NO. 6), which is consistent with the ability of this peptide to block the class II MHC binding of both toxins. Induction of TNFα by SEA, TSST-1, and SEA(121–149), but not LPS was affected; therefore, the antisera must specifically recognize not only the peptide to which it was made, but the corresponding region on the native SEA molecule, as well as a homologous region on TSST-1. Both toxins presumably exhibit structurally similar regions important for TNFα induction. While binding is required for function, it is not sufficient. For example, the N-terminal peptide SEA(39–66) (SEQ ID NO. 2) inhibits SEA binding, but it does not induce monokine production. Only amino acids 121–149 of SEA appear to assume the appropriate conformation to both bind MHC and elicit monokine induction.

Use of synthetic peptide agonists and antagonists rather than the whole superantigen molecule offers advantages such as a lack of side effects and targeting of immune system components. More importantly, specific amino acid residues can be easily and rapidly modified to allow for generation of more effective agonists or antagonists. A peptide agonist, especially of T cell function, is highly unexpected. As a condition of agonist activity, the peptide must bind to MHC, and thus compete for binding with the native SEA molecule.

The peptides claimed according to the subject invention include the specific peptides exemplified herein as well as equivalent peptides which may be, for example, somewhat longer or shorter than the peptides exemplified herein. For example, using the teachings provided herein, a person skilled in the art could readily make peptides having 1 to about 15 or more amino acids added to, or removed from, either end of the disclosed peptides. Preferably, any added amino acids would be the same as the corresponding amino acids of the SEA molecule. Such a longer or shorter peptide would be within the scope of the subject invention as long as said peptide is shorter than the full length SEA molecule and said longer or shorter peptide retains substantially the same relevant biological activity as the peptides exemplified herein. For example, a longer or shorter variation of SEA(121–149) (SEQ ID NO. 6) would fall within the scope of the subject invention as long as said variation retained the ability to activate T cells and to stimulate IL-1 and TNFα production from monocytes. Also within the scope of the subject invention are peptides which have the same amino acid sequences of a peptide exemplified herein except for amino acid substitutions which do not significantly reduce the biological activity. Such substitutions may be, for example, conservative amino acid substitutions which do not affect the ability of the peptide to, for example, stimulate T cell proliferation. As described herein, the peptide sequences of the subject invention can also be the basis for producing peptide antagonists. These antagonists are also within the scope of the subject invention.

Inhibition or antagonism of SEA function without agonist activity can be accomplished through the use of anti-peptide antibodies or modification of residues within the peptide itself. An especially productive means for generation of peptide antagonists has been substitution of L-amino acids with D-amino acids. The efficacy of this approach has been well characterized in the generation of arginine vasopressin analogs with selectively enhanced antidiuretic antagonism by appropriate substitution of L- with D-amino acids (Manning, M., W. H. Sawyer [1985] In: *Vasopressin*, Schrier, R. W., ed., Raven Press, New York, pp. 131–144). Further, not only can antagonism be produced with D-amino acid substitutions, but this antagonism can be directed toward a specific function. This targeting is desirable for superantigen antagonism because of the numerous superantigen activities. The binding affinity/avidity and specific activity our agonist and antagonist peptides can be further enhanced through chemical synthesis of multivalent forms of the agonist and/or antagonist peptides of superantigen activity. Production of potent antagonist peptides will be of value in protection from superantigen-induced disease.

In addition to their use in treating various disease states, the peptides of the subject invention are also useful for stimulating T cells in vitro. This can be important, for example, in a variety of diagnostic procedures. Also, SEA(83–104) (SEQ ID NO. 4) can be used to stimulate production of IL-1 and TNFα.

A further aspect of the claimed invention is the use of the claimed peptides to produce antibodies. These antibodies can be produced using standard procedures well known to those skilled in the art.

The teachings provided herein can be used by those skilled in the art to locate agonist peptides from other superantigens such as SEB, SEC, SED, SEE, and TSST-1.

Materials and Methods

Reagents. SEA was obtained from Toxin Technology (Sarasota, Fla.). Lipopolysaccharide (LPS) (*Escherichia coli* serotype O26:B6) was obtained from Sigma Chemical Co. (St. Louis, Mo.). Fluorescein conjugated mouse anti-human CD14 monoclonal antibody was purchased from Pharmingen (San Diego, Calif.). Recombinant human TNFα was provided by Dr. Nancy Bigley (Wright State University, Dayton, Ohio). Rabbit anti-human TNFα polyclonal antibody and the human IL-1 test kit were purchased from Genzyme (Boston, Mass.).

Figure 1:
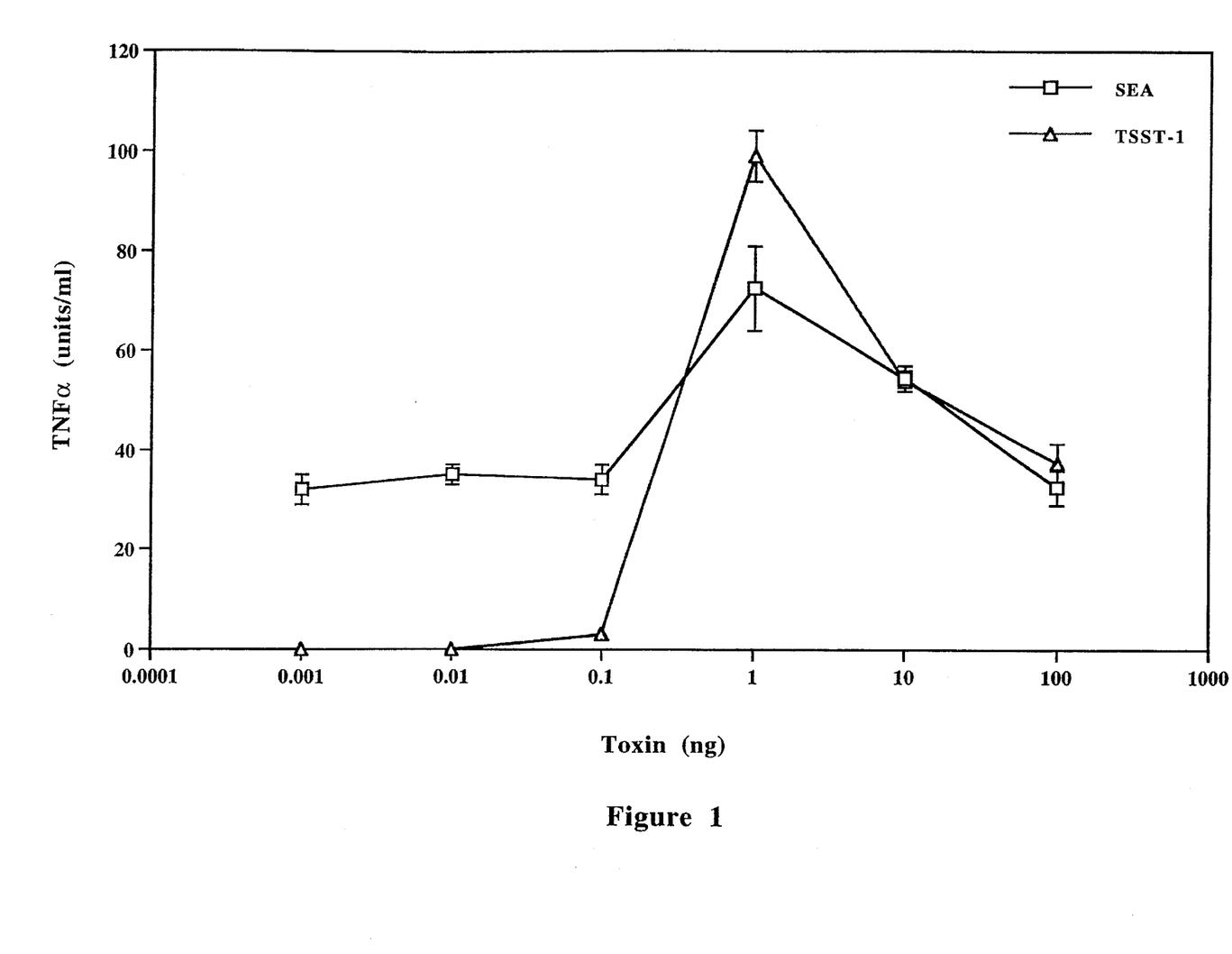
FIG. 1. SEA and TSST-1 induced TNFα production. PBMC ($5 \times 10^5$ cells/well) were stimulated with various concentrations ng/ml of SEA and TSST-1. After 96 hours, supernatant fluids were collected and TNFα activity assessed by cytotoxicity on L-929 cells. Representative results from one of four replicate experiments are expressed as mean units/ml of TNFα activity of triplicate determinations±standard deviation.
Figure 2:
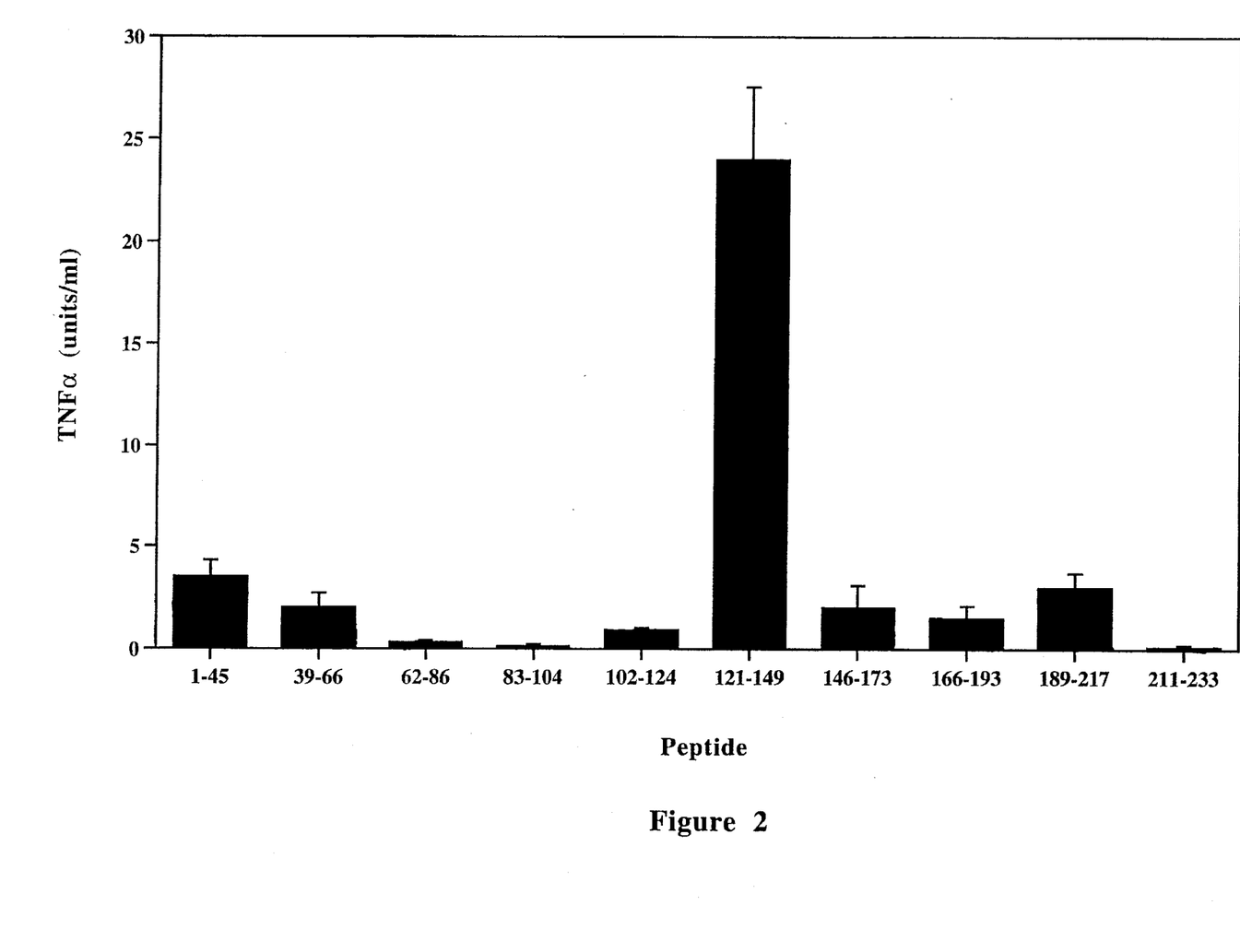
FIG. 2. SEA peptide-induced TNFα production. PBMC were stimulated with 100 μM of each SEA peptide for 18 hours. The supernatant fluids were collected and TNFα activity assessed by cytotoxicity on L-929 cells. Representative results from one of three replicate experiments are expressed as mean units/ml of TNFα activity of triplicate determination±standard deviation. Significant differences were assessed by analysis of variance (p<0.05) followed by Scheffé's multiple comparison test.
Figure 3:
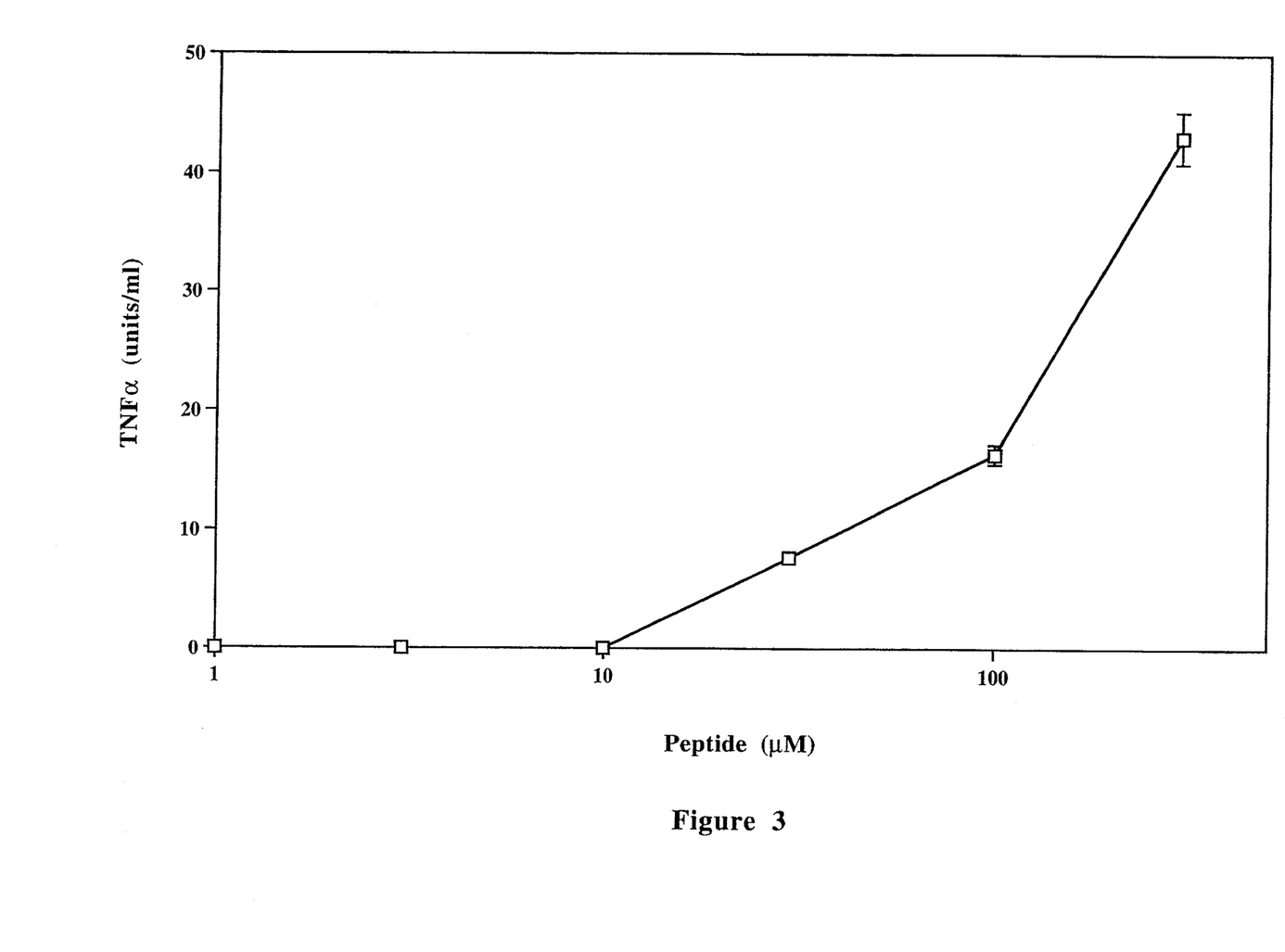
FIG. 3. Dose-response for SEA(121-149) induction of TNFα. PBMC were stimulated with various concentrations of SEA(121-149) for 96 hours, and the supernatant fluids assayed for TNFα activity. Representative results from one of our replicate experiments are expressed as mean units/ml of TNFα of triplicate determinations±standard deviation.

Synthetic peptides. Overlapping peptides corresponding to the entire region of SEA, amino acids 1–45, 39–66, 62–86, 83–104, 102–124, 121–149, 146–173, 166–193, 189–217, and 211–233 (SEQ ID NOS. 1, 2, 3, 4, 5, 6, 7, 8, 9, and 10, respectively) were synthesized with a Biosearch 9500AT automated peptide synthesizer using $N^{\alpha}$-fluoroenylmethyloxycarbonyl chemistry (Chang, C. D., J. Meienhofer [1978] *Int. J. Peptide Protein Res.* 11:246). The amino acid sequence and numbering for each of the synthetic peptides was based on the complete amino acid sequence of Staphylococcal enterotoxin A. This amino acid sequence is well known in the art. See, for example, Griggs, N. D., C. H. Pontzer, M. A. Jarpe, H. M. Johnson [1992] *J. Immunol.* 148:2516. Peptides were cleaved from the resins using trifluoroacetic acid/ethanediol/thioanisole/anisole at a ratio of 90/3/5/2. The cleaved peptides were then extracted in ether and ethyl acetate and subsequently dissolved in water and lyophilized. Reverse phase HPLC analysis of crude peptides indicated one major peak in each profile. Hence, further purification was not warranted. Amino acid analysis of these peptides showed that the amino acid composition corresponded closely to theoretical. Polyclonal antisera to peptides were produced by hyperimmunization of rabbits. For immunization, peptides were conjugated to keyhole limpet hemocyanin using glutaraldehyde as the coupling reagent.

Class II MHC binding. Human peripheral blood mononuclear cells were obtained from healthy volunteers by centrifugation over Ficoll-hypaque. The population was enriched for adherent cells by plastic adherence. Adherent cells ($1\times10^6$) were washed with phosphate buffered saline (PBS) and incubated with 50 μl of FACS buffer (PBS containing 10 mM sodium azide and 0.5% bovine serum albumin) or 10 μM SEA at 37° C. for 40 minutes. After incubation, each tube received 50 μl of 300 μM biotinylated SEA(121–149) and was incubated for an additional 40 minutes. For biotinylation, 10 mg of SEA(121–149) were dissolved in 50 mM bicarbonate buffer (pH=9.6) with 0.2 mg of NHS-LC-biotin (Pierce) and incubated on ice for 2 hours. Unreacted biotin was removed by dialysis. The cells were washed twice with FACS buffer and further incubated with 50 μl of streptavidin-phycoerythrin (Becton Dickinson, Mountain View, Calif.) at 1 μg/ml for 15 minutes at 4° C. and washed two more times. Monocytes were identified by double labeling with fluorescein conjugated anti-human CD14. Cells were analyzed by flow cytometry (FACStar; Becton Dickinson), and fluorescence is expressed as relative intensity.

Cytokine production. Human peripheral blood mononuclear cells (PBMC; $5\times10^5$ cells/well) were added to 96-well plates in 200 μl RPMI 1640 containing 10% fetal bovine serum. Cells were stimulated with various concentrations of SEA, TSST-1, LPS, and SEA peptides. After 18 or 96 hours, supernatant fluids were collected and assayed for TNFα activity. For antibody inhibition studies, a 1:100 final dilution of polyclonal rabbit anti-SEA(121–149) was added to each well.

TNFα activity in the culture supernates was assayed on L-929 cells treated with 5 μg/ml actinomycin D and cultured at $2\times10^4$ cells/well in 96-well plates. For estimation of TNFα levels, a standard curve was generated using from 0.1 to 10 units/ml of recombinant human TNFα, and the samples diluted accordingly. After 18 hours at 37° C., the supernates were discarded, and the viable cells stained with crystal violet. The dye was solubilized with SDS, and the optical densities read at 570 nm with a Bio-Rad microplate reader. Identification of TNFα as the cytotoxic agent was performed by the addition of a 1:250 dilution of rabbit anti-human TNFα antibody. IL-1 activity was assessed by competitive radioimmunoassay (Human IL-1α RIA test kit [Genzyme]).

Following are examples which illustrate procedures, including the best mode, for practicing the invention. These examples should not be construed as limiting. All percentages are by weight and all solvent mixture proportions are by volume unless otherwise noted.

Example 1 - Staphylococcal Enterotoxin-Induced TNFα Production

Human PBMC were stimulated with 0.001 to 100 ng of SEA or TSST-1 for 96 hours (FIG. 1). Both toxins induced significant TNFα production. While TSST-1 induced higher levels of TNFα at a concentration of 1 ng/ml, SEA was effective over a broader range. The cytotoxic activity was primarily attributable to TNFα since addition of anti-TNFα antibody neutralized 63% and 76% of the SEA and TSST-1 activity, respectively. A similar pattern was observed at 18 hours, although lower amounts of TNFα were produced. TNFα production by monocytes depleted of T cells induced by 1 ng/ml of both toxins was reduced from 73 and 99 units/ml for SEA and TSST-1, respectively, to approximately 25 units TNFα/ml at 96 hours. This is consistent with the T cell requirement for toxin-induced monokine production (Fischer et al., supra; Gjörloff et al., supra).

Example 2 - Peptide-Induced TNFα Production

Ten overlapping synthetic peptides representing the SEA sequence were added to human PBMC, and the resultant TNFα activity assessed. FIG. 2 shows that one peptide, SEA(121–149), induced significant TNFα production. The cytotoxic activity was a function of TNFα because it could be neutralized 90% by anti-TNFα antisera (Table 1).

TABLE 1

Anti-TNFα inhibition of peptide-induced TNFα

| Peptide | No antibody | Anti-TNFα |
|---|---|---|
| SEA(1–45)(SEQ ID NO. 1) | 3.30 ± 0.56 | 0.01 ± 0 |
| SEA(39–66) (SEQ ID NO. 2) | 1.95 ± 0.35 | 0 |
| SEA(62–86) (SEQ ID NO. 3) | 0.21 ± 0.04 | 0 |
| SEA(83–104) (SEQ ID NO. 4) | 0.08 ± 0.02 | 0 |
| SEA(102–124) (SEQ ID NO. 5) | 0.60 ± 0.10 | 0 |
| SEA(121–149) (SEQ ID NO. 6) | 24.1 ± 2.95 | 2.41 ± 0.02 |
| SEA(146–173) (SEQ ID NO. 7) | 1.85 ± 0.77 | 0.01 ± 0 |
| SEA(166–193) (SEQ ID NO. 8) | 1.05 ± 0.15 | 0 |
| SEA(189–217) (SEQ ID NO. 9) | 2.15 ± 0.37 | 0.05 ± 0.01 |
| SEA(211–233) (SEQ ID NO. 10) | 0.03 ± 0 | 0 |

*These experiments were performed as described in FIG. 2 except for the addition of a 1:250 dilution of rabbit anti-human TNFα antibody. Representative results from one of three replicate experiments are expressed as mean units/ml of TNFα activity of triplicate determinations ± standard deviation.

TNFα activity was observed by 18 hours, and increased approximately 2-fold by 96 hours. In a dose-response study, cells were stimulated with various concentrations of SEA(121–149) (SEQ ID NO. 6) for 96 hours, and TNFα activity assessed (FIG. 3). SEA(121–149) was effective at a concentration as low as 30 μM. While the native SEA is effective at 0.1–1 nM, SEA(121–149) may not be expected to assume optimal conformation, and other regions acting in concert with 121–149 may account for the higher specific activity of the whole superantigen molecule.

Example 3 - Antibody Inhibition of TNFα Production

Figure 4:
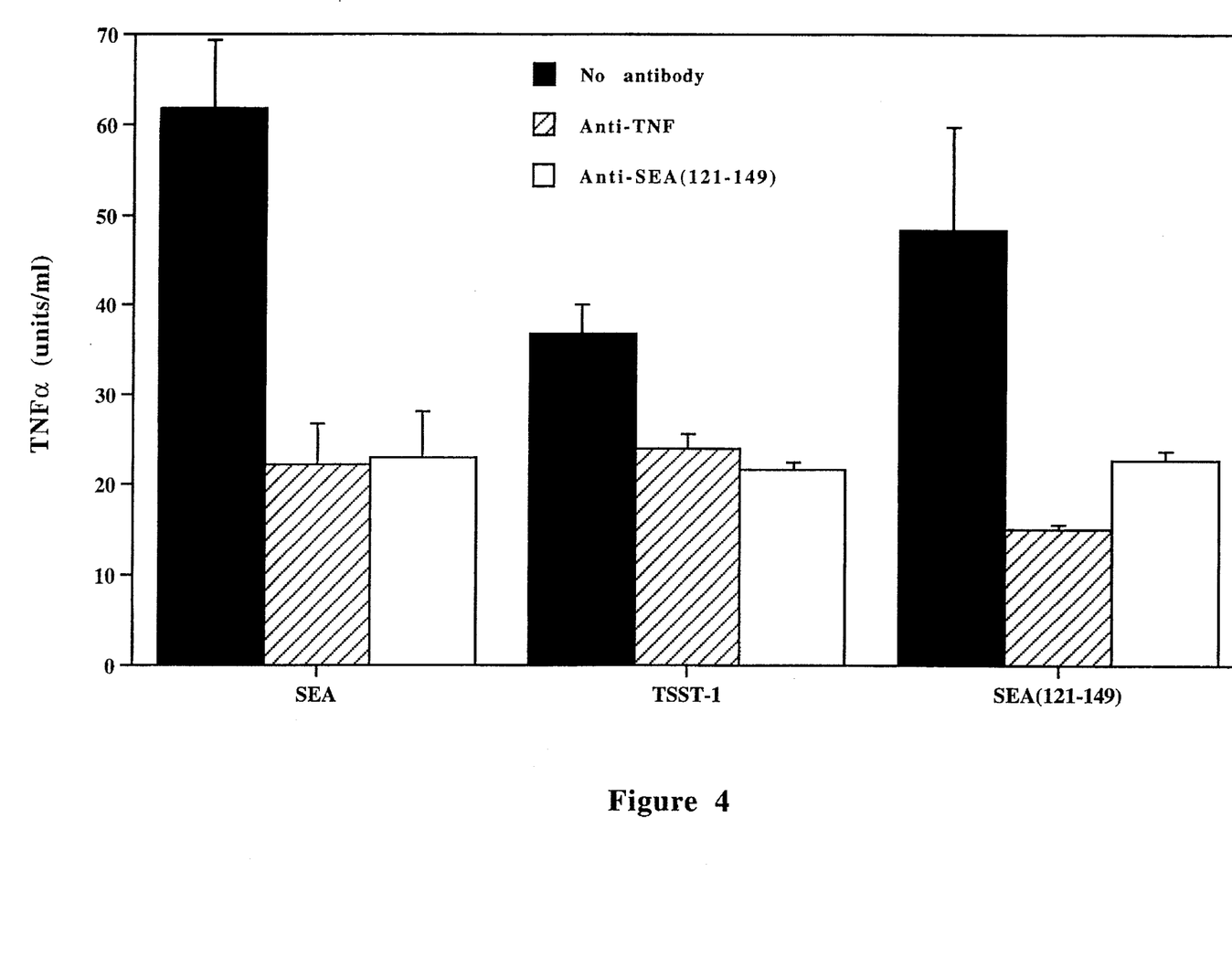
FIG. 4. Antibody inhibition of TNFα production. PBMC were stimulated with 100 ng/ml SEA or TSST-1 or 100 μM SEA(121-149) for 96 hours, and TNFα activity was assessed. Polyclonal rabbit anti-SEA(121-149) was added at a 1:100 final dilution, and rabbit anti-human TNFα antibody was added at a 1:250 final dilution. No antibody was equivalent to addition of nonimmune sera. Representative results from one of three replicate experiments are expressed as mean units/ml of TNFα activity of triplicate determinations±standard deviation.
Figure 5:
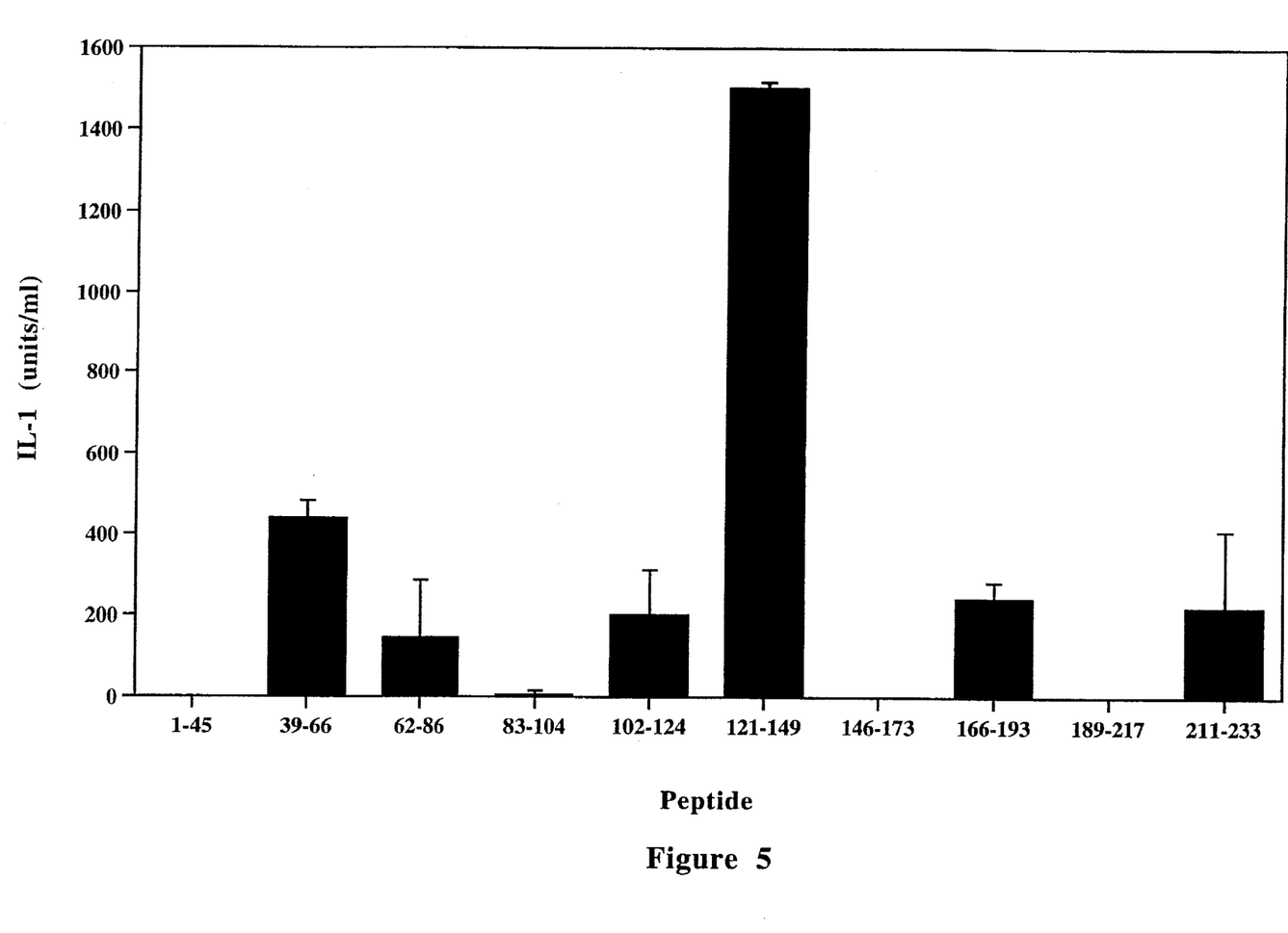
FIG. 5. SEA peptide induced IL-1 production. The experiments were performed as described in FIG. 2. IL-1 activity was assessed by competitive radioimmunoassay. Representative results from one of two replicate experiments are expressed as mean units/ml of IL-1 activity±standard deviation.

Addition of polyclonal anti-human TNFα antisera to PBMC cultures stimulated with either toxins or toxin peptide significantly reduced cytotoxic activity of the supernatant fluids on L-929 cells by neutralizing TNFα activity (FIG. 4). Further, addition of polyclonal anti-SEA(121–149) (SEQ ID NO. 6) antisera inhibited TNFα production to about the same extent, indicating almost complete reduction of TNFα production. Induction of TNFα by SEA, TSST-1, and SEA(121–149) were all affected; therefore, the antisera must recognize not only the peptide to which it was made, but the corresponding region on the native SEA molecule, as well as a homologous region on TSST-1. In contrast, induction of TNFα by LPS was unaffected by anti-SEA(121–149) antisera, indicating the specificity of the response.

Example 4 - SEA Peptide IL-1 Production

The panel of SEA peptides was also examined for their ability to stimulate IL-1 secretion. The same peptide, SEA(121–149) (SEQ ID NO. 6), induced over 1,400 units of IL-1 activity at 18 hours. No IL-1 production was observed in the absence of peptide, and 100 ng/ml SEA (4 mM) induced 875±5 units/ml of IL-1 activity.

Example 5 - Binding of SEA(121–149) (SEQ ID NO. 6) to Human Monocytes

Figure 6A:
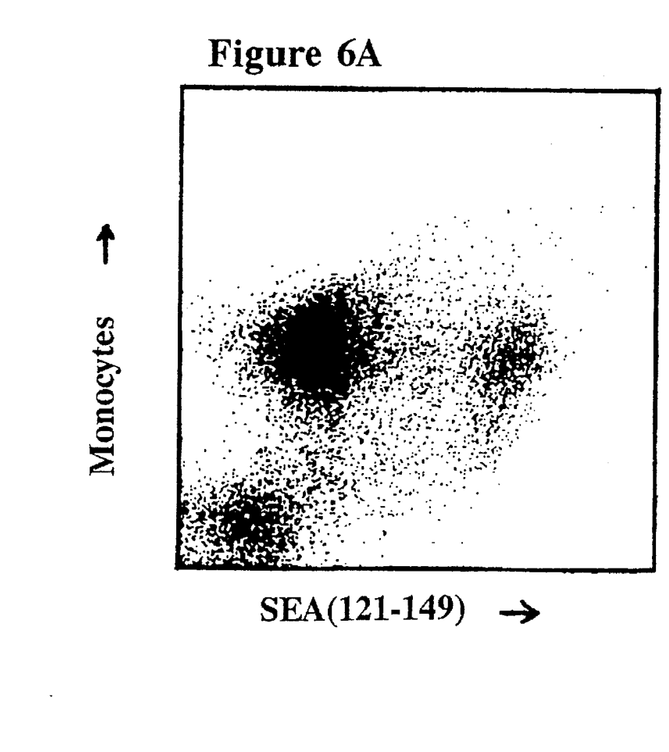
FIG. 6A and 6B. Binding of SEA(121-149) to human monocytes. Plastic adherent cells (1×10⁶) were preincubated with 50 μl of either FACS buffer (FIG. 6A) or 10 μM SEA (FIG. 6B) at 37° C. for 40 minutes. Biotinylated SEA(121-149) was added at a final concentration of 300 μM, and the mixture was incubated for an additional 40 minutes. Cells were washed and labeled with streptavidin-phycoerythrin. Monocytes were identified by double labeling with fluorescein conjugated anti-human CD14. Cells were analyzed by flow cytometry, and the results of one of three replicate experiments are presented as two parameter fluorescence histograms of green versus red fluorescence intensity.
Figure 6B:
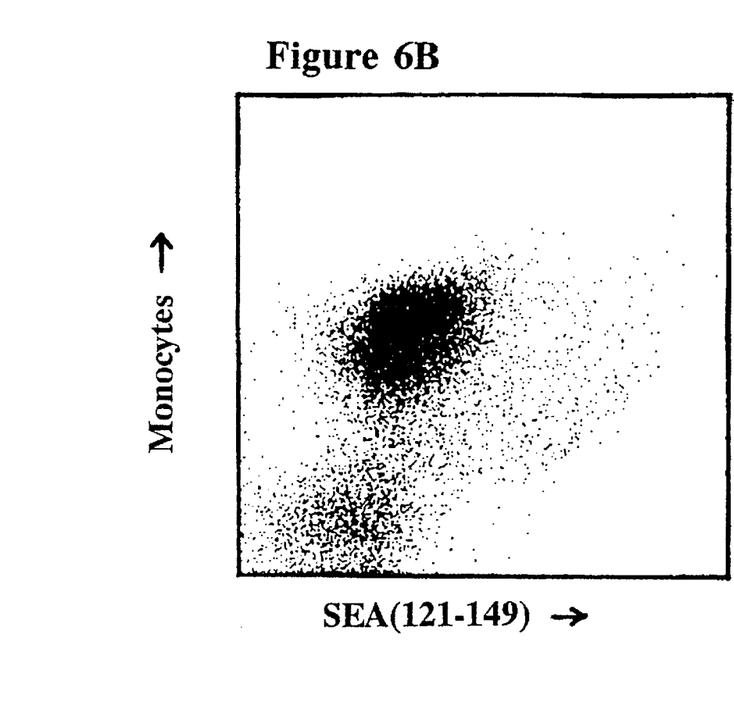

PBMC were enriched for monocytes by plastic adherence, and 300 μM of biotinylated SEA(121–149) (SEQ ID NO. 6) was added in the absence or presence of 10 μM SEA. Approximately 90% of the cells were identified as monocytes by double labeling with fluorescein conjugated anti-human CD14. The labeled peptide SEA(121–149) bound directly to a subpopulation of monocytes, and its binding was specifically inhibited by native SEA (FIG. 6A and 6B). This suggests that SEA(121–149) binds to SEA superantigen binding sites on the MHC molecule.

It should be understood that the examples and embodiments described herein are for illustrative purposes only and that various modifications or changes in light thereof will be suggested to persons skilled in the an and are to be included within the spirit and purview of this application and the scope of the appended claims.

We claim:

1. A peptide which consists of an amino acid sequence selected from the group consisting of the amino acid sequences shown in SEQ ID NO. 2, SEQ ID NO. 4, and SEQ ID NO. 6.

2. The peptide, according to claim 1, wherein said peptide consists of the amino acid sequence shown in SEQ ID NO. 2.

3. The peptide, according to claim 1, wherein said peptide consists of the amino acid sequence shown in SEQ ID NO. 4.

4. The peptide, according to claim 1, wherein said peptide consists of the amino acid sequence shown in SEQ ID NO. 6.

* * * * *

UNITED STATES PATENT AND TRADEMARK OFFICE
CERTIFICATE OF CORRECTION

PATENT NO. : 5,545,716

DATED : August 13, 1996

INVENTOR(S) : Howard M. Johnson, Carol H. Pontzer, and Nathan D. Griggs

It is certified that error appears in the above-indentified patent and that said Letters Patent is hereby corrected as shown below:

Column 1: Line 25: "[ 1988]" should read --[1988]--; Line 37: "[1989]" should read --[1989]--. (no bold)

Column 2: Line 26: "antigem" should read --antigen--.

Column 4: Line 45: "(12 - 149)," should read --(121 - 149),--.

Column 6: Line 56: "(121-149)" should read --(121-149)-- (no bold); Line 63: "$V_\beta 5a^+ T$ and $V_\beta 8^+$ T" should read --$V_\beta 5a^+$ and $V_\beta 8^+$ T--; Lines 63-64: "$V8^+$ SEA sensitive $V\beta$ elements." should read --SEA sensitive $V\beta$ elements.--.

Column 7: Line 59: "121-149" should read --121-149--. (no bold)

Column 12: Line 25: "an" should read --art--.

Signed and Sealed this

Twenty-first Day of January, 1997

Attest:

BRUCE LEHMAN

Attesting Officer

Commissioner of Patents and Trademarks